United States Patent
Meslovich et al.

(10) Patent No.: US 9,745,176 B2
(45) Date of Patent: Aug. 29, 2017

(54) METHOD FOR RETRIEVING STORAGE RACKS FROM A TANK FREEZER USING A RETRIEVAL CRANE, AND RELATED COMBINATIONS

(71) Applicant: Fisher BioServices Inc., Rockville, MD (US)

(72) Inventors: Susan Murphy Meslovich, Walkersville, MD (US); Erman Mandaci, Rockville, MD (US)

(73) Assignee: Fisher BioServices Inc., Rockville, MD (US)

(*) Notice: Subject to any disclaimer, the term of this patent is extended or adjusted under 35 U.S.C. 154(b) by 616 days.

(21) Appl. No.: 14/272,953

(22) Filed: May 8, 2014

(65) Prior Publication Data
US 2015/0321888 A1    Nov. 12, 2015

(51) Int. Cl.
  *B66C 23/48*    (2006.01)
  *F25D 3/10*    (2006.01)
  *F25D 25/00*    (2006.01)
  *G01N 1/42*    (2006.01)

(52) U.S. Cl.
  CPC ............. *B66C 23/48* (2013.01); *F25D 3/105* (2013.01); *F25D 25/00* (2013.01); *G01N 1/42* (2013.01)

(58) Field of Classification Search
  CPC ..... B66C 23/166; B66C 23/48; B66C 23/485; B66C 1/701; F25D 25/00; F25D 3/105; G01N 1/42
  See application file for complete search history.

(56) References Cited

U.S. PATENT DOCUMENTS

| | | | | |
|---|---|---|---|---|
| 264,865 A | * | 9/1882 | De Voe | F25D 25/00 62/378 |
| 316,840 A | * | 4/1885 | Shaw | F25D 25/00 312/312 |
| 319,840 A | * | 6/1885 | Shaw | B29C 45/00 24/51 |
| 1,380,779 A | * | 6/1921 | Craig | B66C 23/48 212/345 |
| 1,920,989 A | * | 8/1933 | Layhon | B66C 23/48 212/343 |
| 4,969,336 A | | 11/1990 | Knippscheer et al. | |
| 5,125,240 A | | 6/1992 | Knippscheer et al. | |
| 5,595,451 A | | 1/1997 | Harrison, Jr. | |

(Continued)

*Primary Examiner* — Sang Kim
*Assistant Examiner* — Nathaniel Adams
(74) *Attorney, Agent, or Firm* — Wood Herron & Evans LLP (57) ABSTRACT

A method for retrieving storage racks in a tank freezer includes positioning a retrieval crane adjacent to the tank freezer such that a base of the retrieval crane is positionable underneath a bottom wall of a tank body. The retrieval crane includes a boom extending upwardly and laterally outwardly over the base so that a retention hook at a free end of a cable associated with the boom may be extended or retracted relative to the tank freezer. More specifically, the cable may be moved to extend the hook through the opening of the tank freezer into a storage space, and then retract the hook to lift and then hold a selected storage rack in a hoisted position. The method avoids the use of manual hoisting of storage racks, and the retrieval crane may be used with any of a plurality of similar tank freezers located in a larger facility.

10 Claims, 10 Drawing Sheets

(56) References Cited

U.S. PATENT DOCUMENTS

| | | |
|---|---|---|
| 5,918,861 A * | 7/1999 | Parker .................... B66C 23/48 212/202 |
| 5,921,102 A | 7/1999 | Vago |
| 6,941,762 B2 | 9/2005 | Felder et al. |
| 7,540,168 B2 | 6/2009 | Schumann et al. |
| 7,596,957 B2 | 10/2009 | Fuhr et al. |
| 7,861,540 B2 | 1/2011 | Cloutier et al. |
| 7,918,093 B2 | 4/2011 | Dillon et al. |
| 8,099,967 B2 | 1/2012 | Jia |
| 8,176,747 B2 | 5/2012 | Howard et al. |
| 2008/0168626 A1 | 7/2008 | Sewell |
| 2011/0088424 A1 | 4/2011 | Cloutier et al. |
| 2012/0060514 A1 | 3/2012 | Warhurst et al. |
| 2012/0060520 A1 | 3/2012 | Collins et al. |
| 2012/0060539 A1 | 3/2012 | Hunt et al. |
| 2012/0060541 A1 | 3/2012 | Hunt et al. |

\* cited by examiner

METHOD FOR RETRIEVING STORAGE RACKS FROM A TANK FREEZER USING A RETRIEVAL CRANE, AND RELATED COMBINATIONS

TECHNICAL FIELD

The present invention relates generally to hoisting devices and methods, and more particularly, to a crane used in conjunction with a tank freezer, as well as methods for using the crane with a plurality of tank freezers.

BACKGROUND

Cold storage units such as freezers are used for various purposes, including the storage of biological samples over short and long periods of time. For example, biological materials for transplantation such as blood, tissue, or plasma may require storage for short periods of time before use. In another example, biological cells such as DNA samples may be stored for longer periods of time. Conventional cold storage units may be cooled by mechanical refrigeration circuits or by other methods, including the provision of liquid nitrogen ("LN2"). One type of cold storage unit used to store biological samples is tank or chest storage freezers (hereinafter collectively referred to as "tank freezers"), which include a relatively large storage area accessed through an opening formed at a top end of the tank or chest. The storage area is filled with storage racks which may be pulled vertically out of the storage area through the opening to access the samples stored in the storage rack.

Conventional tank freezers are typically large in height, requiring steps or a stool to be provided for an operator to gain access to the opening at the top of the tank. As a result of the large size of these tank freezers, it can be difficult to reach into the storage area and have enough leverage, especially while standing on steps or on a stool, to lift and hold the storage rack at a particular height during retrieval of a desired sample from the storage rack.

Moreover, storage facilities for biological samples, for example, typically maintain a plurality of tank freezers. It will be understood that each separate biological sample that must be retrieved by an operator could be located in separate tank freezers, which necessitates repeated climbing and arduous work of lifting the pertinent storage racks out of each of the tank freezers. If an automated assist mechanism is provided to help open a door of the tank freezer or hold the storage rack, such automated assist mechanisms are typically permanently mounted on or about the tank freezer, thereby significantly increasing the space taken up by each of the tank freezers within a facility as well as significantly increasing the cost and maintenance needs for each tank freezer.

There is a need, therefore, for an apparatus and method that further simplifies the retrieval and storage process for storage racks located inside tank freezers.

SUMMARY OF THE INVENTION

The present invention overcomes the foregoing and other shortcomings and drawbacks of tank freezers and associated methods heretofore known. While the invention will be described in connection with certain embodiments, it will be understood that the invention is not limited to these embodiments. On the contrary, the invention includes all alternatives, modifications and equivalents as may be included within the spirit and scope of the present invention.

To this end, the present invention provides a method for retrieving storage racks in a tank freezer, when the tank freezer includes a storage space defined by a tank body having a bottom wall spaced from a floor surface by at least one support, a sidewall extending upwardly from the bottom wall, and a top wall defining an opening into the storage space. The method includes positioning a retrieval crane adjacent to the tank freezer such that a base of the retrieval crane is located on the floor surface and extends at least partially underneath the bottom wall of the tank body. The retrieval crane includes a boom that extends upwardly and laterally over the base to an upper terminal end of the boom, and a cable running along at least a portion of the boom such that the cable is extendible or retractable to move a retention hook located at a free end of the cable relative to the upper terminal end of the boom. The method also includes extending the cable to lower the retention hook through the opening in the tank freezer and attaching the retention hook to a selected one of the storage racks within the storage space. The cable is then retracted to lift the retention hook and the selected storage rack through the opening and to a hoisted position at least partially out of the tank freezer. As a result, the lifting and hoisting of the storage rack is performed automatically so that the user can focus on removing and replacing storage boxes into the storage racks, and the retrieval crane is advantageously usable with any number of similar tank freezers.

In one embodiment, the method also includes locking the cable in position to maintain the selected storage rack in the hoisted position while items, such as samples, are retrieved from or placed into the storage rack. The retrieval crane also includes wheels connected to the base in some embodiments, which means positioning the retrieval crane further includes rolling the base and at least one of the wheels between the bottom wall and the floor surface. The wheels are mounted on the base with a low profile so that the wheels and at least a portion of the base can collectively fit underneath the bottom wall of the tank freezer. When a locking brake is associated with at least one of the wheels, the wheels are locked with the at least one locking brake after rolling the base between the bottom wall and the floor surface. The locking brake maintains the position of the retrieval crane by preventing rolling movement of the wheels relative to the tank freezer during use of the cable and the retention hook.

The retention hook and the cable may be moved relative to the upper terminal end of the boom using different actuating mechanisms depending on the specific embodiment chosen. For example, when the opposite end of the cable (relative to the free end with the retention hook) is wound about a reel connected to a hand crank, the hand crank is rotated to wind up or unwind the cable and thereby move the free end of the cable towards or away from the upper terminal end of the boom. If the free end of the cable has reached a desirable stationary position, such as at the hoisted position with the storage rack held by the retention hook, then a locking mechanism may be engaged with the hand crank to prevent further rotation of the hand crank in either direction until the locking mechanism is disengaged. To this end, the user can be assured that the hoisted storage rack will remain in position during his or her work. Alternatively, the opposite end of the cable (relative to the free end with the retention hook) may be wound about a reel associated with an electric winch, in which case the electric winch is actuated to wind up or unwind the cable. The electric winch typically inherently locks the position of the cable when inactive, as well.

As described above, the retrieval crane may advantageously be used with different tank freezers in the same facility. In this regard, the method also includes extending the cable to lower the retention hook and the selected storage rack through the opening back into the storage space and detaching the retention hook from the selected storage rack such that the retrieval crane is ready for use for another storage rack. The cable may be retracted again towards the upper terminal end of the boom before moving the retrieval crane. The retrieval crane is then moved away from the first tank freezer to be located adjacent to a second tank freezer containing a second selected storage rack to be retrieved. Once the retrieval crane is in position adjacent to the second tank freezer, the method includes inserting the free end of the cable and the retention hook into the storage space of the second tank freezer to prepare the second selected storage rack to be hoisted out of the storage space. Therefore, the single retrieval crane may be used to retrieve and hoist storage racks in any number of a plurality of tank freezers.

In order to help assist a user in moving the retrieval crane about a facility with multiple tank freezers, a set of handles may be provided so as to project laterally outward from a generally vertical frame member that extends between the base and boom of the retrieval crane. The user pushes or pulls the pair of handles until the retrieval crane is located in a desired position adjacent to a tank freezer, with the upper terminal end of the boom located directly above the opening in the tank freezer. The entire retrieval crane is formed to have a light weight, such as a weight of less than 50 pounds, to help make the movement of the crane between the tank freezers easy for an operator, especially when the base includes wheels. In some alternative embodiments, the boom is connected to the vertical frame member by a pivoting joint, and the method may further include ratcheting this pivoting joint to rotate the boom relative to the base. This rotation adjusts how far the base has to be inserted underneath the bottom wall of the tank freezer in order to position the upper terminal end of the boom directly over the opening in a tank freezer, which is the operational position of the retrieval crane.

In another aspect of the present invention, a combination of a plurality of tank freezers and a retrieval crane is provided. Each of the tank freezers includes a storage space defined by a tank body including a bottom wall spaced from a floor surface by at least one support, a sidewall extending upwardly from the bottom wall, and a top wall defining an opening into the storage space. The retrieval crane includes a base, a boom extending upwardly and laterally over the base to an upper terminal end, and a cable running along at least a portion of the boom. The cable is thus extendible or retractable relative to the upper terminal end of the boom to move a retention hook located at a free end of the cable. As described above, the base is sized for insertion underneath the bottom wall of each of the tank freezers so that the retrieval crane can be positioned adjacent to any one of the tank freezers with the upper terminal end of the boom directly above the opening of that tank freezer. As such, this combination enables retrieval of storage racks from each of the plurality of tank freezers using the retrieval crane.

In yet another aspect of the present invention, a retrieval crane is configured to be used to lift storage racks contained in one or more storage freezers. The crane includes a base having a plurality of wheels connected to the base, at least one of the wheels being at least partially recessed inside the base. As a result, the wheels and base collectively define a base height that is configured to fit underneath a storage freezer when the crane is positioned at the storage freezer. The crane also includes a frame member extending upwardly from the base and a winch coupled to the frame member, a boom coupled to the frame member and extending laterally upwardly and laterally over the base, and a cable. The cable extends from a first end associated with the winch, through at least a portion of the frame member and the boom, to a free end carrying a retention hook which extends from and is located below an upper terminal end of the boom.

These and various additional aspects and features of the present invention will become more readily apparent to those of ordinary skill upon review of the following detailed description taken in conjunction with the drawings of the exemplary embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

It should be understood that the appended drawings are not necessarily to scale, presenting a somewhat simplified representation of various preferred features illustrative of the basic principles of the invention. The specific design features of the retrieval crane and tank freezers as disclosed herein, including, for example, specific dimensions, orientations, locations, and shapes of various illustrated components, will be determined in part by the particular intended application and use environment. Certain features of the illustrated embodiments may have been enlarged or distorted relative to others to facilitate visualization and clear understanding.

DETAILED DESCRIPTION

FIGS. 1 through 4 illustrate a first exemplary embodiment of a retrieval crane 10 in accordance with the present invention, the retrieval crane 10 being configured to assist with hoisting and holding storage racks which are to be pulled generally vertically from large tank freezers. The specific interaction of the retrieval crane 10 of this embodiment with a plurality of tank freezers is described in further detail with respect to the method shown in FIGS. 5 through 9 below. However, FIGS. 1 through 4 are intended to provide additional details regarding the retrieval crane 10 itself. The retrieval crane 10 is lightweight and easy to move so that the crane 10 can be used with any of a plurality of tank freezers located in a facility, and the crane 10 avoids the need for a human user to perform the lifting or hoisting steps when removing a storage rack from a tank freezer. The portable nature of the crane 10 allows this solution to be applicable to facilities of all sizes (e.g., facilities having one or a few tank freezers, as well as those having a large plurality of tank freezers).

Figure 1:
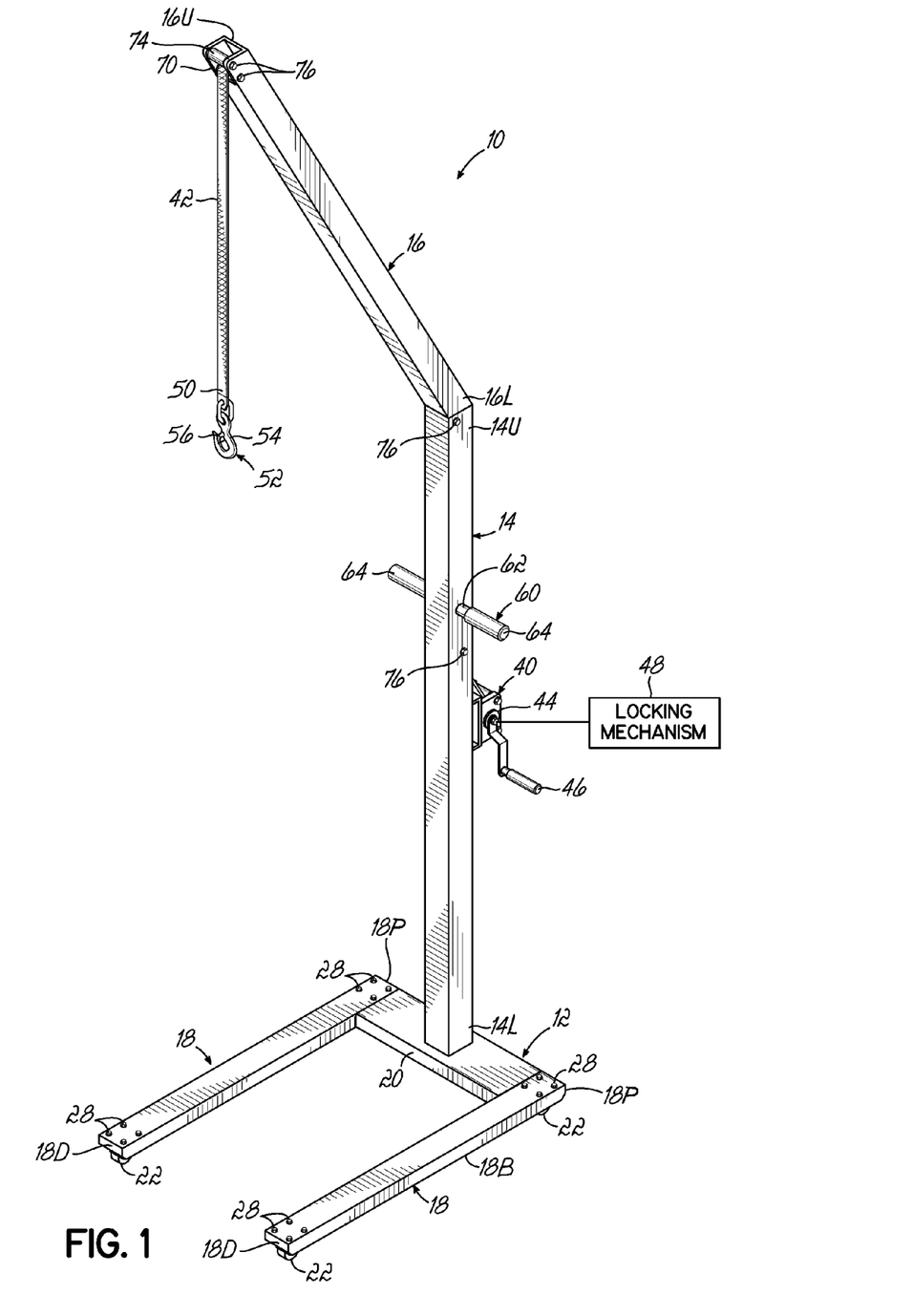
FIG. 1 is a front top perspective view of a retrieval crane used in a method of retrieving storage racks from tank freezers, in accordance with a first exemplary embodiment of the present invention.
Figure 2:
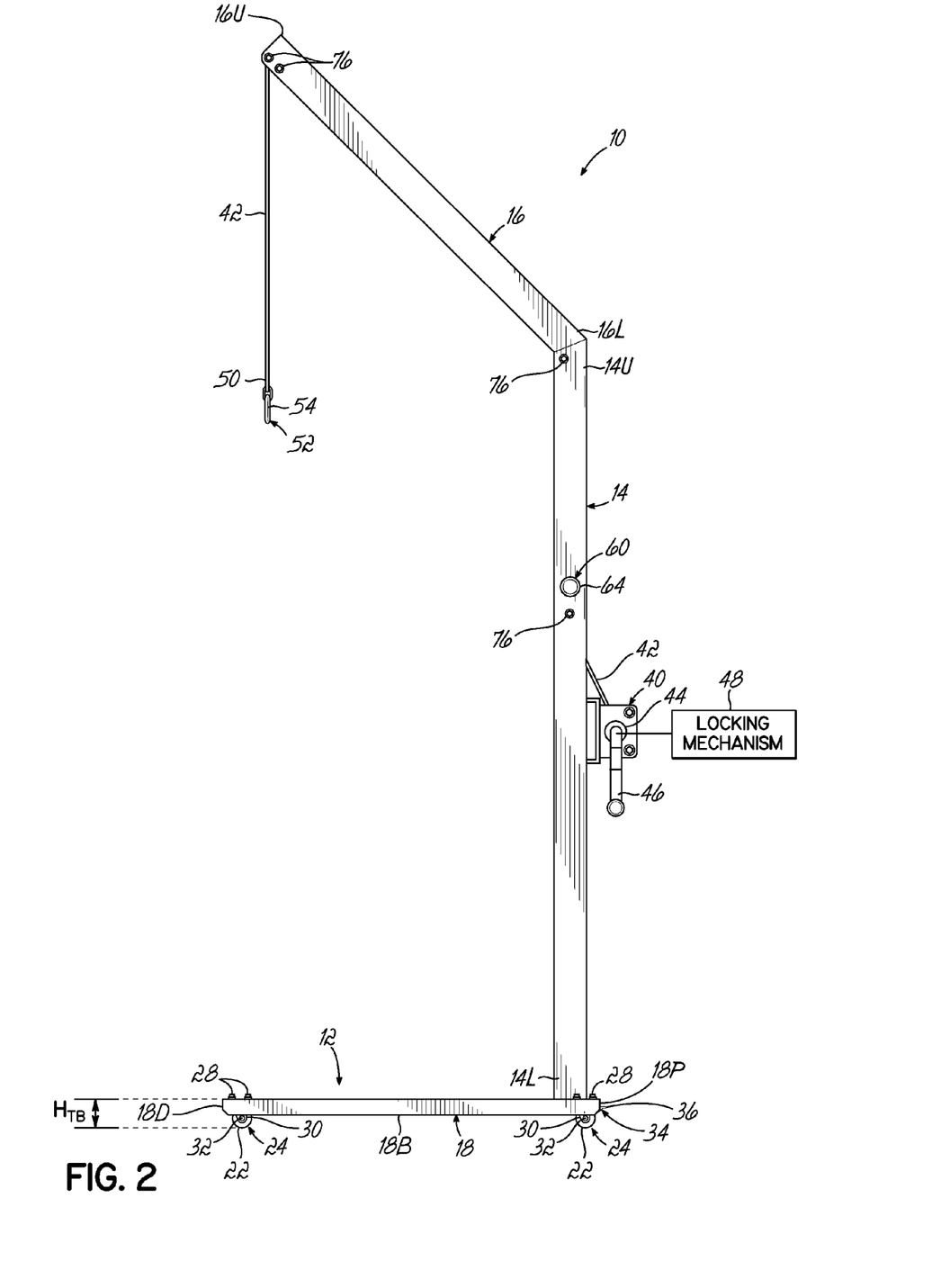
FIG. 2 is a side elevation view of the retrieval crane of FIG. 1, showing how a boom of the crane extends upwardly and laterally over a base of the crane.

With particular reference to FIGS. 1 and 2, the retrieval crane 10 includes a base 12, a generally vertical frame member 14 extending upwardly from the base 12, and a boom 16 extending upwardly and laterally from the vertical frame member 14. More specifically, the base 12 is a generally U-shaped member defined by two parallel base members 18 connected at one end by a transverse base member 20. It will be understood that the "parallel" base members 18 may also be splayed in a non-parallel orientation in other embodiments depending on the preferences of the end user. In other embodiments, only a single base member 18 may be provided. The base 12 is configured to be low profile or relatively small in height, even when including caster wheels 22 as shown, so as to fit underneath the tank freezers, as described in further detail below.

The vertical frame member 14 is typically centered along the transverse base member 20 and extends from a lower terminal end 14L connected to the transverse base member 20 to an upper terminal end 14U coupled to the boom 16. Similarly, the boom 16 includes a lower terminal end 16L coupled to the vertical frame member 14 and an upper terminal end 16U positioned to extend above and laterally over an area defined by the base 12. As a result, when the crane 10 is positioned adjacent to a tank freezer with the parallel base members 18 extending at least partially underneath the tank freezer, the upper terminal end 16U of the boom 16 will be located directly above the tank freezer. Moreover, any loads acting on the upper terminal end 16U of the boom 16 that would tend to cantilever about the base 12 are supported without causing a tipping over of the crane 10. However, the particular relative position of the boom 16 and the base 12 on the crane 10 may be modified in other embodiments without departing from the present invention.

The base 12, vertical frame member 14, and boom 16 collectively define the framework for the retrieval crane 10. In one embodiment, these elements 12, 14 and 16 are each manufactured from aluminum and welded together at the corresponding junctions to generate a generally lightweight structure. Furthermore, the base 12 is formed from generally flat sheet members (which may be bent into U-shaped members as described below with reference to the parallel base members 18) while the larger vertical frame member and boom 16 are defined by generally hollow beams to reduce the overall weight of the crane 10. For example, the framework of the crane 10 weighs about 30 to 35 pounds in the exemplary embodiment made from aluminum materials. This amount of weight, especially when mounted upon the wheels 22, renders the crane 10 easy for essentially all users to move around a facility as needed. It will be understood that other types of materials such as steel may be used for the framework, and other types of fastening arrangements between the base 12, the vertical frame member 14, and the boom 16 may be used in other embodiments while remaining in accordance with the present invention.

Figures 3, 3A:
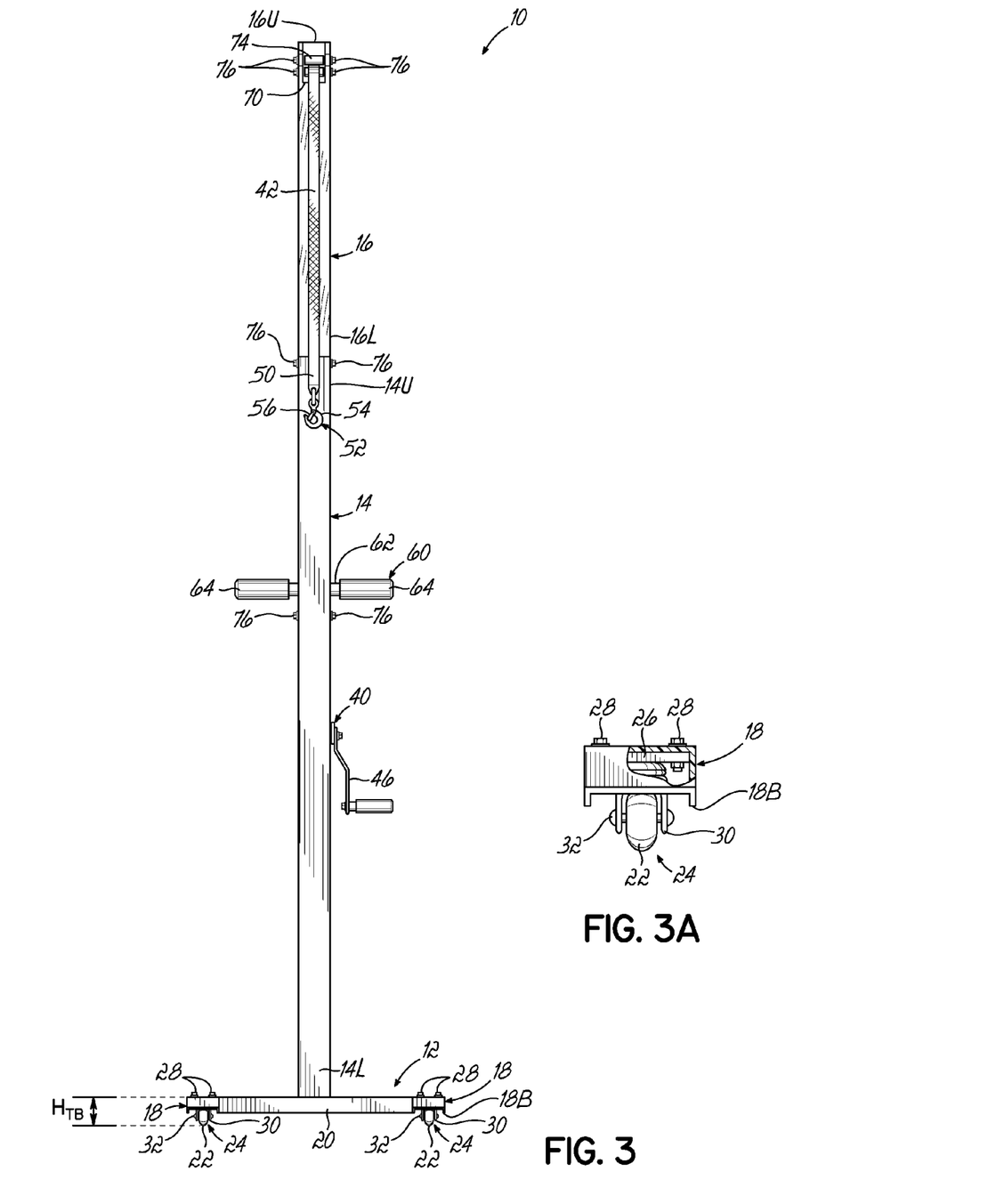
FIG. 3 is a front elevation view of the retrieval crane of FIG. 2, showing a pair of handles and a hand crank extending laterally from a generally vertical frame member that extends between the boom and the base.
FIG. 3A is an expanded detail front view of a portion of the base and one wheel assembly shown in FIG. 3, with the base partially cut away to reveal additional aspects of the wheel assembly.

As described above, the base 12 in this embodiment is defined by two parallel base members 18 connected by the transverse base member 20. Although the plurality of base members 18, 20 is shown as separate elements connected together by welding or the like in this embodiment, it will be understood that the base 12 could be integrally formed from a single generally flat piece of material in other embodiments. Returning to the embodiment shown in FIG. 1, each of the parallel base members 18 includes a proximal end 18P connected to the transverse base member 20 and a distal end 18D configured to be rolled underneath the tank freezer. The wheels 22, or more specifically, wheel assemblies 24 are connected to the base 12 adjacent to each of the proximal ends 18P and each of the distal ends 18D, thereby providing four corner support for the base 12. In this regard, the wheel assemblies 24 include top plates 26 that are mounted to the underside of the parallel base members 18 using a plurality of fasteners 28 as shown in FIGS. 1 and 3A. These fasteners 28 may be bolts or screws, for example. The parallel base members 18 and the wheel assemblies 24 are configured such that the wheels 22 are mounted at least partially recessed into the interior of the parallel base members 18 as shown in FIGS. 2 and 3. To this end, a bottom edge 18B of the parallel base members 18 is located at a lower elevation than a top of the wheels 22 when the wheel assemblies 24 are coupled to the base 12 so that the full diameter of the wheels 22 are not located beneath the bottom edge 18B of the parallel base member 18. For example, the parallel base member 18 may be formed with a U-shaped hollow cross section as shown in FIG. 3A, for example. This at least partial recessing of the wheels 22 into the base 12 provides a low profile for the base 12 that enables rolling movement of the base 12 and wheels 22 underneath a tank freezer, as described in further detail below. Moreover, all of the wheels 22 or a partial subset of the wheels 22 may be recessed at least partially into the base in various embodiments of the present invention.

As shown most clearly in FIGS. 2 through 3A, each of the wheel assemblies 24 also includes axle supports 30 extending downwardly from the top plate 26, and an axle 32 extending between the axle supports 30 and through the center of the corresponding wheel 22. One example of such a wheel assembly 24 is commercially available as the Translucent Skate Wheel Caster from www.CoolCasters.com, for example, which includes 2.5-inch diameter wheels 22 and are capable of supporting a load of about 110 pounds per wheel 22. Nevertheless, it will be understood that other caster wheels and other types of wheel assemblies may be used with the base 12 in any number and positioning relative to the base 12 in other embodiments (and also that the wheels 22 may be free to rotate about a vertical axis to function as actual casters, in some embodiments).

At least the two wheel assemblies 24 located at the back end of the crane 10 (e.g., at the proximal ends 18P of the parallel base members 18) also include a locking brake 34 coupled to the axle supports 30 and configured to be moved between an unlocked position spaced from the wheels 22 and a locked position in frictional engagement with the wheels 22. To this end, the locking brakes 34 include a brake handle 36 that extends beyond the proximal ends 18P of the parallel base members 18 so that a user can readily move the locking brakes 34 between the two positions, such as with his or her foot. The locking brakes 34 prevent or at least strongly discourage rotation of the wheels 22, which causes the retrieval crane 10 to be maintained in a stationary position, such as after placement adjacent to the tank freezer. Consequently, the crane 10 is less likely to be dislodged from the desired position during use at a tank freezer.

As described above, when the wheels 22 are provided on the base 12 as shown in FIG. 3A, the wheels 22 are at least partially recessed into the interior of the parallel base members 18. That type of recessed mounting of the wheels 22 enables the combination of the base 12 and wheels 22 to remain as low profile (e.g., as small in height) as possible. For example, the combination of the base 12 and the wheels 22 may define a total base height $H_{TB}$ of less than 5.0 inches, in the exemplary embodiment, which is designed to fit underneath a tank freezer. Alternatively, the wheels 22 on the base 12 could also be replaced with low-friction feet or other supports (not shown), such as downwardly extending corner feet coated with a polytetrafluoroethylene material, in other embodiments. Such alternative supports may also enable easy movement of the retrieval crane 10 to various different tank freezers, although it will be understood that a different type of or no locking mechanism/brake may be provided in such alternative embodiments. Regardless of the particular support(s) extending downwardly from the base 12, the crane 10 is configured to have the base 12 positioned at least partially underneath a freezer tank when in use at the freezer tank.

The vertical frame member 14 is a hollow aluminum beam defining a generally square-shaped cross section along the entire length from the lower terminal end 14L to the upper terminal end 14U. About halfway along the length of the vertical frame member 14 in the exemplary embodiment, the crane 10 also includes an actuator, such as a manual winch 40 configured to control movements of a cable 42 associated with the crane 10. As described in further detail below, the cable 42 of this embodiment includes a nylon weave strap extending from a reel 44 at the manual winch 40 through portions of the vertical frame member 14 and boom 16 to the upper terminal end 16U of the boom 16. In the exemplary embodiment, the nylon weave strap of the cable 42 and the manual winch 40 are configured to handle loads of up to 600 pounds during operation of the crane 10.

The manual winch 40 also includes a hand crank 46 connected to the reel 44 and projecting laterally outward from one side of the manual winch 40 (and also beyond the lateral extent of the vertical frame member 14). Rotations of the hand crank 46 cause rotations of the reel 44, which leads to winding up or unwinding of the cable 42 as well as movement of the cable 42 relative to the upper terminal end 16U of the boom 16. To this end, the hand crank 46 controls operation of the manual winch 40 and the cable 42 in the retrieval crane 10, although it will be understood that other automated mechanisms could be used in other embodiments. Furthermore, the manual winch 40 may also include a locking mechanism 48 which may be selectively engaged with the hand crank 46 to prevent movement of the hand crank 46 in either rotational direction, such as when the cable 42 has lifted a storage rack to a desired position and a user wants to keep the storage rack in this position until he or she is done working on the storage rack. This locking mechanism 48 is shown schematically in FIG. 1 as it will be understood that various mechanisms may be used to stop movements of the hand crank 46, including, but not limited to, locking pins or arms engaged with stationary structure on the manual winch 40, or a clamp-like member selectively capturing the hand crank 46 in a certain rotational orientation or position.

The cable 42 or strap in this exemplary embodiment extends from a free end 50 which hangs below the upper terminal end 16U of the boom to an opposite end (not shown) fixedly coupled to the reel 44. Thus, as the hand crank 46 is rotated by a user to wind up the cable 42, the free end 50 of the cable 42 will move upwardly or retract towards the upper terminal end 16U of the boom 16. Likewise, as the hand crank 46 is rotated by a user to unwind the cable 42, the free end 50 of the cable 42 will drop with gravity or extend away from the upper terminal end 16U. This gravitational drop is assisted by connecting a retention hook 52 onto the free end 50 of the cable. The retention hook 52 is typically formed from a brass material capable of withstanding up to 500 pound loads, although other materials and types of retention hooks may be used in other embodiments. As shown in FIGS. 1 through 3, the retention hook 52 includes the typical J-shaped hook member 54 defining an opening and a clasp arm 56 pivotally coupled to the J-shaped hook member 54 and configured to selectively open and close the opening. A user is able to easily attach and decouple this retention hook 52 from handles on a storage rack or any other structure that is to be lifted using the retrieval crane 10.

A small distance above the manual winch 40, the crane 10 further includes a pair of handles 60 projecting in opposite transverse directions from opposing sides of the vertical frame member 14. Each of the handles 60 includes a generally cylindrical handle bar 62 manufactured from steel or aluminum and welded into contact with the vertical frame member 14, and also a rubberized grip sleeve 64 slid over the length of the cylindrical handle bar 62. For example, in the exemplary embodiment the rubberized grip sleeve 64 includes a ribbed surface and is configured to snugly fit over a ⅞ inch diameter cylindrical handle bar 62 over a length of about 4.75 inches of that cylindrical handle bar 62. However, it will be understood that the particular dimensions and materials used to form the handle bars 62 and the grip sleeves 64 may be modified in other exemplary embodiments, or the grip sleeves 64 may be omitted from the handle bars 62 in still other embodiments. The pair or set of handles 60 is conveniently located at a height above the base 12 that is within normal reach for substantially all users when standing next to the retrieval crane 10, and the handles 60 are configured to be pushed or pulled to help move the crane 10 around a facility and into position adjacent to a tank freezer. In this regard, the handles 60 help the user improve control of movements of the crane 10 between uses of the cable 42 and manual winch 40.

Returning with reference to FIG. 1, the boom 16 is fixedly coupled, such as by welding, at the lower terminal end 16L to the upper terminal end 14U of the vertical frame member 14. The boom 16 is angled at this connection so that along the length of the boom 16 to the upper terminal end 16U, the boom 16 projects upwardly from the vertical frame member 14 and laterally over an area defined by the base 12. Like the vertical frame member 14, the boom 16 is manufactured as a hollow, generally square-shaped cross section aluminum beam running between the respective lower and upper terminal ends 16L, 16U. Of course, the particular shape, size, and materials used to form the boom 16 can be modified in accordance with other embodiments of the present invention, just as with the base 12 and the vertical frame member 14. The boom 16 also includes a cable opening 70 located adjacent the upper terminal end 16U as shown in FIG. 1. This cable opening 70 allows the cable 42 to run through the interior of the boom and then exit the framework at the upper terminal end 16U of the boom 16. As a result, the free end 50 of the cable 42 and the retention hook 52 hang generally directly underneath the upper terminal end 16U of the boom 16. More details regarding the path of the cable 42 through the retrieval crane 10 are provided with reference to FIG. 4 below.

As shown in FIGS. 2 and 3, the boom 16 is angled relative to the vertical frame member 14 to such an extent that the upper terminal end 16U of the boom 16 is located at a centralized location in a transverse direction (e.g., between the parallel base members 18 and in line with the vertical frame member 14). The upper terminal end 16U of the boom 16 is also located directly above a point located between the proximal and distal ends 18P, 18D of the parallel base members 18 as well. Accordingly, the four-corner support provided at the base 12 by the wheels 22 is capable of withstanding bending moments and forces that may be applied in any direction from the upper terminal end 16U of the boom 16 without tending to tip over the retrieval crane 10. To this end, the boom 16 and the remainder of the framework of the crane 10 do not form an overall cantilevered arrangement in the exemplary embodiment, although the boom 16 could be modified to be pivotable relative to the remainder of the frame as described in further detail below, which could lead to a slight cantilever arrangement in some operating states. In the exemplary embodiment, this structural arrangement of the base 12 and the boom 16 enables the free end 50 of the cable 42 to be arranged above an opening in a top wall of a tank freezer when the base 12 is partially rolled underneath the bottom wall of the tank freezer. This leads to an intuitive positioning and use of the crane 10 for users.

Figure 4:
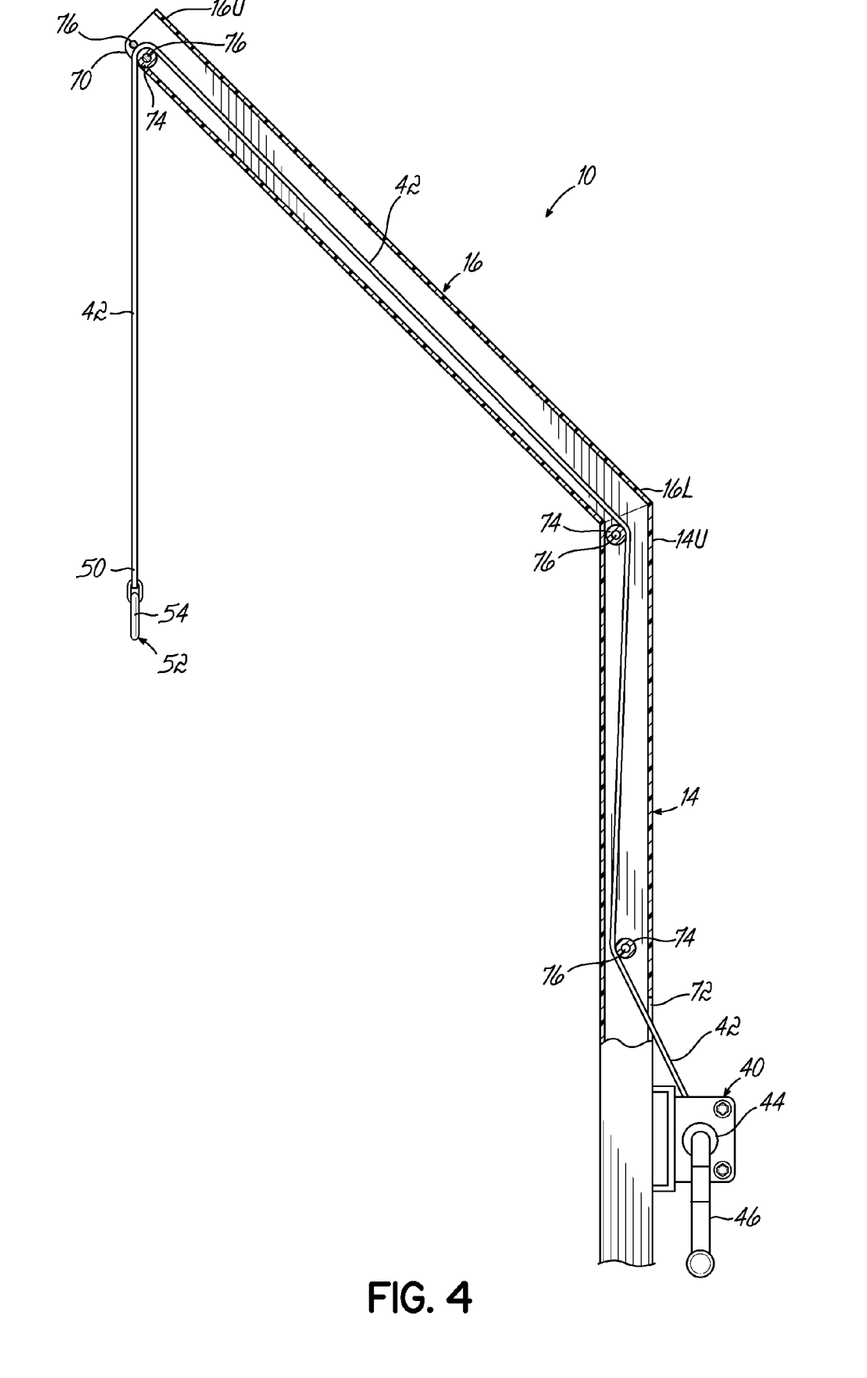
FIG. 4 is a partially cross-sectioned side view of the retrieval crane of FIG. 2, with portions of the boom and the vertical frame member sectioned so as to reveal the path of the cable within the retrieval crane.

Turning with reference to FIG. 4, the vertical frame member 14 and the boom 16 are shown at least partially cross-sectioned to reveal internal structures and the path of the cable 42 in the exemplary embodiment of the retrieval crane 10. The vertical frame member 14 also includes a cable opening 72 located on a rear or proximal side between the set of handles 60 and the manual winch 40, this cable opening 72 enabling the cable 42 to run from outside the framework (at the manual winch 40) to inside the hollow interior of the vertical frame member 14. To this end, with the exception of the working portion of the cable 42 near the free end 50 and the portion of the cable stored on the reel 44 of the manual winch 40, the cable 42 is run completely along and within the interior of the vertical frame member 14 and the boom 16. As a result, the cable 42 is highly unlikely to be tangled up in or caught on other structures as the crane 10 moved about the facility, and a user is not likely to be pinched by any portion of the cable 42 as it moves relative to the crane 10.

In order to avoid unwanted frictional contact with bent edges within the vertical frame member 14 or the boom 16, the crane 10 includes interior structures in the form of a plurality of bearing members 74 mounted on bolt fasteners 76 (which may be secured by nuts as shown and as well understood) in FIG. 4. In one embodiment, the bearing members 74 are stationary cylinders formed from or coated with a low-friction material such as polytetrafluoroethylene, while in another embodiment, the bearing members 74 are rotating bearings that are free to rotate about the bolt fasteners 76 extending through the center of the bearing members 74. In either potential embodiment, the rounded contour of the bearing members 74 avoids any sharp edges that the cable 42 could ride against as it moves within the interior of the vertical frame member 14 and the boom 16. The bearing members 74 also may act as idlers or tensioners between the retention hook 52 and the reel 44 in some embodiments. At a minimum, the bearing members 74 are positioned to guide the cable 42 along a desired path between the cable opening 70 in the boom 16 and the cable opening 72 in the vertical frame member 14.

In the exemplary embodiment, the bearing members 74 are located as follows. One bearing member 74 is located in the vertical frame member 14 generally just above the cable opening 72 and just below the handles 60. This bearing member 74 guides the cable 42 into the vertical frame member 14 and avoids a frictional contact with any sharp edges that may be defined at the cable opening 72. A second bearing member 74 is also located in the vertical frame member 14, but this one is near the upper terminal end 14U of the vertical frame member 14. This second bearing member 74 guides the cable 42 to move from the vertical frame member 14 into the boom 16 without frictionally rubbing against the angled edge defined between these elements. It will be understood that this bearing member 74 (or any others) may be repositioned, such as for example, by being placed in the lower terminal end 16L of the boom 16 instead of in the vertical frame member 14.

A third bearing member 74 is located in the upper terminal end 16U of the boom 16 adjacent to the cable opening 70 at that location. This third bearing member 74 therefore prevents frictional contact of the cable 42 with any sharp edge that may be formed at the cable opening 70 in the boom 16. The cable 42 may be threaded between two bearing members 74 (or a bearing member 74 and a bolt fastener 76, as shown in FIG. 4) near this cable opening 70 to avoid the frictional contact with sharp edges and also to help prevent excessive retraction of the cable 42 with the manual winch 40. To this end, the cable 42 will likely be blocked by further movement when the retention hook 52 tries to move between the bearing members 74 at the cable opening 70 in the boom 16. Thus, by providing two bearing members 74 or the arrangement shown in FIG. 4, the crane 10 avoids pulling the retention hook 52 back into the boom 16 where it cannot be accessed or used.

With reference to FIGS. 5 through 9, a method for using the retrieval crane 10 according to the exemplary embodiment in combination with a plurality of tank freezers 80, 80a stored in a facility is shown in stepwise detail. Each of the tank freezers (80 is the only one shown in FIG. 5) includes a tank body 82 enclosing a storage space 84 configured to receive vertically-oriented storage racks for holding storage boxes and other items, as well understood in the cold storage field. In this regard, the tank body 82 includes a bottom wall 86 spaced from a floor surface 88 by a plurality of supports 90 (legs in the exemplary embodiment, although it will be appreciated that caster wheels and other similar supports may also be used in other embodiments). The tank body 82 also includes a generally cylindrical sidewall 92 extending upwardly from the bottom wall 86 and a top wall 94 defining an opening 96 into the storage space 84 that may be selectively opened and closed by a door 98 pivotally coupled to the top wall 94 by a hinge 100. As described above, the tank freezers 80 that may be used with the retrieval crane 10 may include various types of cooling systems, including forced convection coolant circulation systems as well as passive liquid nitrogen (LN2) cooling systems. Regardless of the particular type of refrigeration mechanism used, the tank freezer 80 requires access through the opening 96 at the top wall 94 and hoisting or lifting of the vertically-oriented storage racks up and out of the storage space 84 whenever items are to be removed from or added to the storage rack. Without the provision of the retrieval crane 10, such removal and holding of the storage racks can be highly physically taxing on a user.

Figure 5:
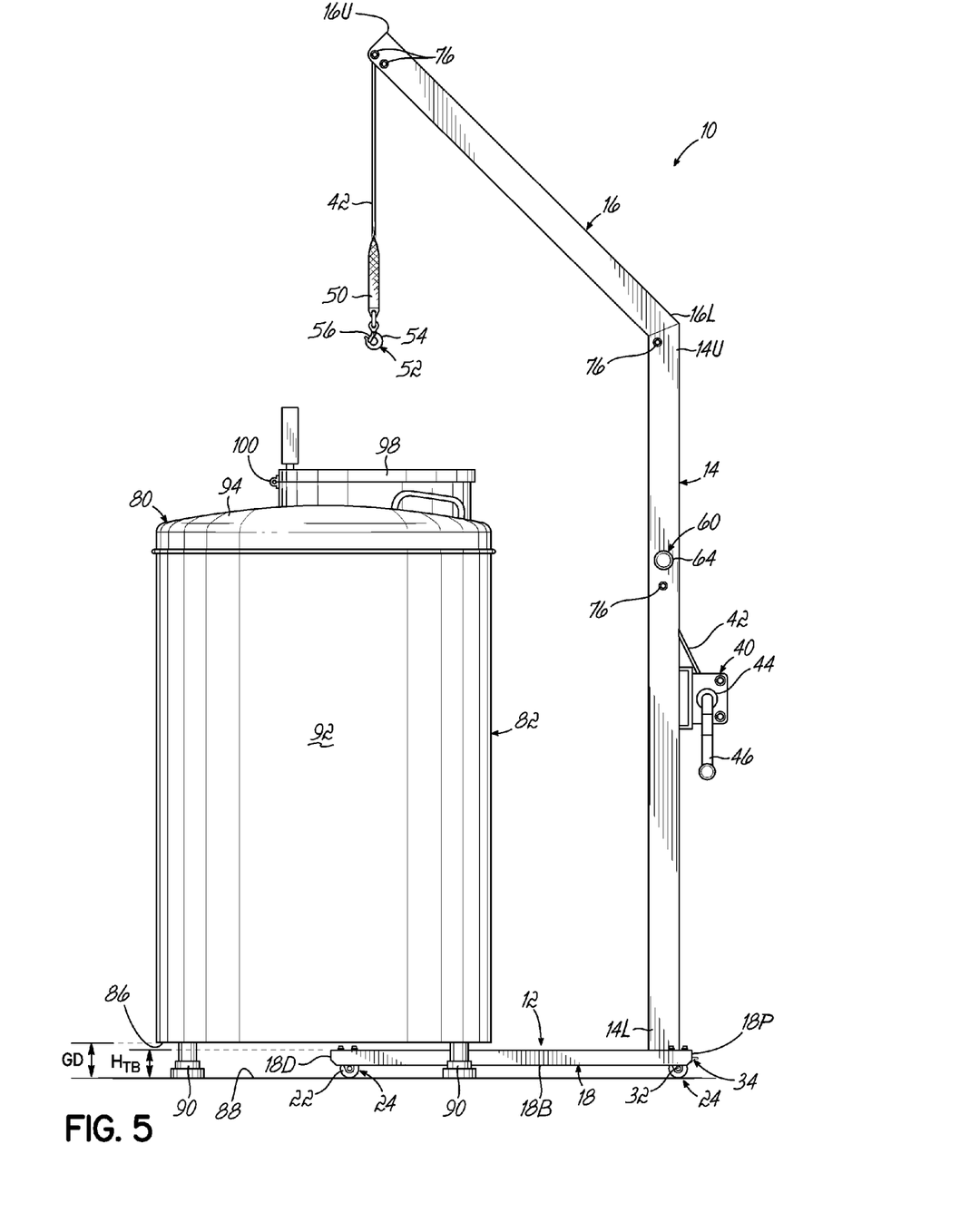
FIG. 5 is a side view of the retrieval crane of FIG. 1 positioned adjacent to a tank freezer according to a first operational state of the method in accordance with the present invention, with the hook located above an opening in the top wall of a tank body of the tank freezer and the base rolled underneath a bottom wall of the tank body.
Figure 6:
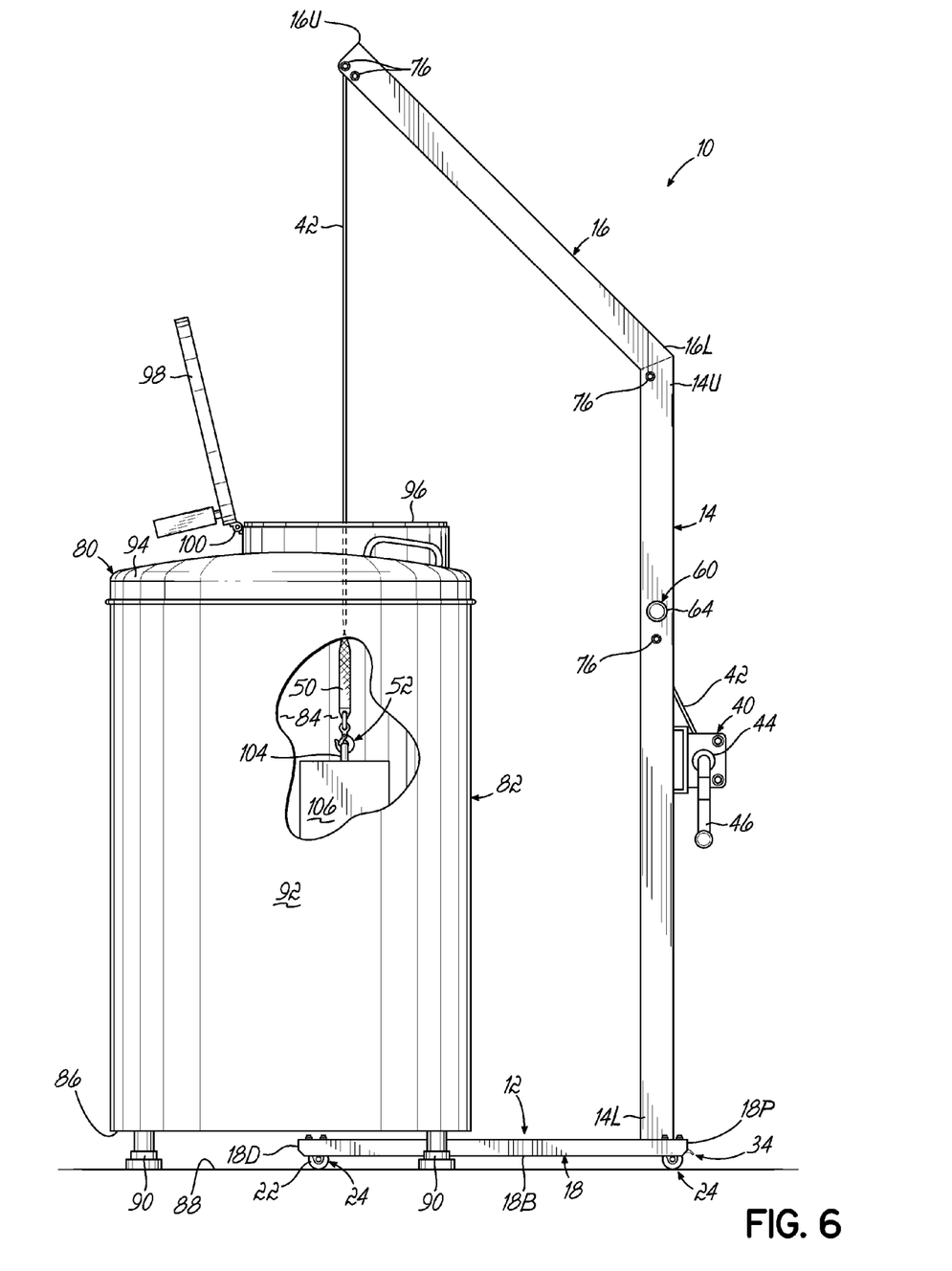
FIG. 6 is a side view of the retrieval crane and tank freezer of FIG. 5 in a second operational state of the method, in which the cable has been extended so that the hook moves through the opening and into the storage space so as to be secured with a handle of a storage rack inside the storage space, as revealed by the partial cutaway shown in a sidewall of the tank body.

A first operational state for retrieving storage racks with the retrieval crane 10 is shown in FIG. 5. In this state, a portion of the base 12, and specifically a portion of the parallel base members 18, have been rolled underneath the bottom wall 86 of the tank freezer 80 so that the crane 10 is positioned adjacent to the tank freezer 80. In this position, it can be more clearly seen that the low profile of the base 12 and wheels 22 enables those portions of the crane 10 to freely move between the bottom wall 86 and the floor surface 88. More specifically, the bottom wall 86 and the floor surface 88 define a clearance or gap distance GD which may be about 5.0 inches in an exemplary embodiment. As described above, the exemplary embodiment of the crane 10 includes a base 12 and wheels 22 that collectively define a total base height $H_{TB}$ of less than 5.0 inches as shown. Once again, the at least partial recessing of the wheels 22 into the parallel base members 18 advantageously provides the low profile at this portion of the crane 10 so as to fit underneath the tank freezer 80. Also in this position, FIG. 5 shows that the free end 50 of the cable 42 and the retention hook 52 are located directly above the door 98 at the opening 96 in the tank freezer 80. Consequently, the retrieval crane 10 is in position for operation at the tank freezer 80. If the position of the crane 10 requires further adjustment, the user may push or pull on the set of handles 60 at the vertical frame member 14 until the upper terminal end 16U of the boom 16 is located above the door 98 and the opening 96 as shown in FIG. 5.

Once the crane 10 is located adjacent to the tank freezer 80 in the desired position, the user may lock some or all of the wheels 22 using the locking brakes 34 associated with those wheels 22. The activated state of the locking brakes 34 is shown, for example, in FIGS. 6 through 8, which reveal the next operational states of the crane 10 and tank freezer 80. In the second operational state shown in FIG. 6, the user has opened the door 98 to provide access to the storage space 84 via the opening 96, and the hand crank 46 has been rotated to extend the free end 50 of the cable 42 and the retention hook 52 downwardly through the opening 96 into the storage space 84. To this end, the rotation of the hand crank 46 unwinds some of the cable 42 off of the reel 44, and the weight of the retention hook 52 pulls the cable downwardly from the upper terminal end 16U of the boom 16 when this unwinding leads to potential slack in the cable 42. Once the retention hook 52 is low enough within the tank freezer 80, the user snaps the retention hook 52 into engagement with a handle 104 (or hook or similar protruding structure) provided on the top of a selected storage rack 106. The sidewall 92 is shown partially cut away in FIG. 6 to reveal this attachment of the retention hook 52 to the storage rack 106. In this position, the selected storage rack 106 is ready to be hoisted out of the storage space 84.

Figure 7:
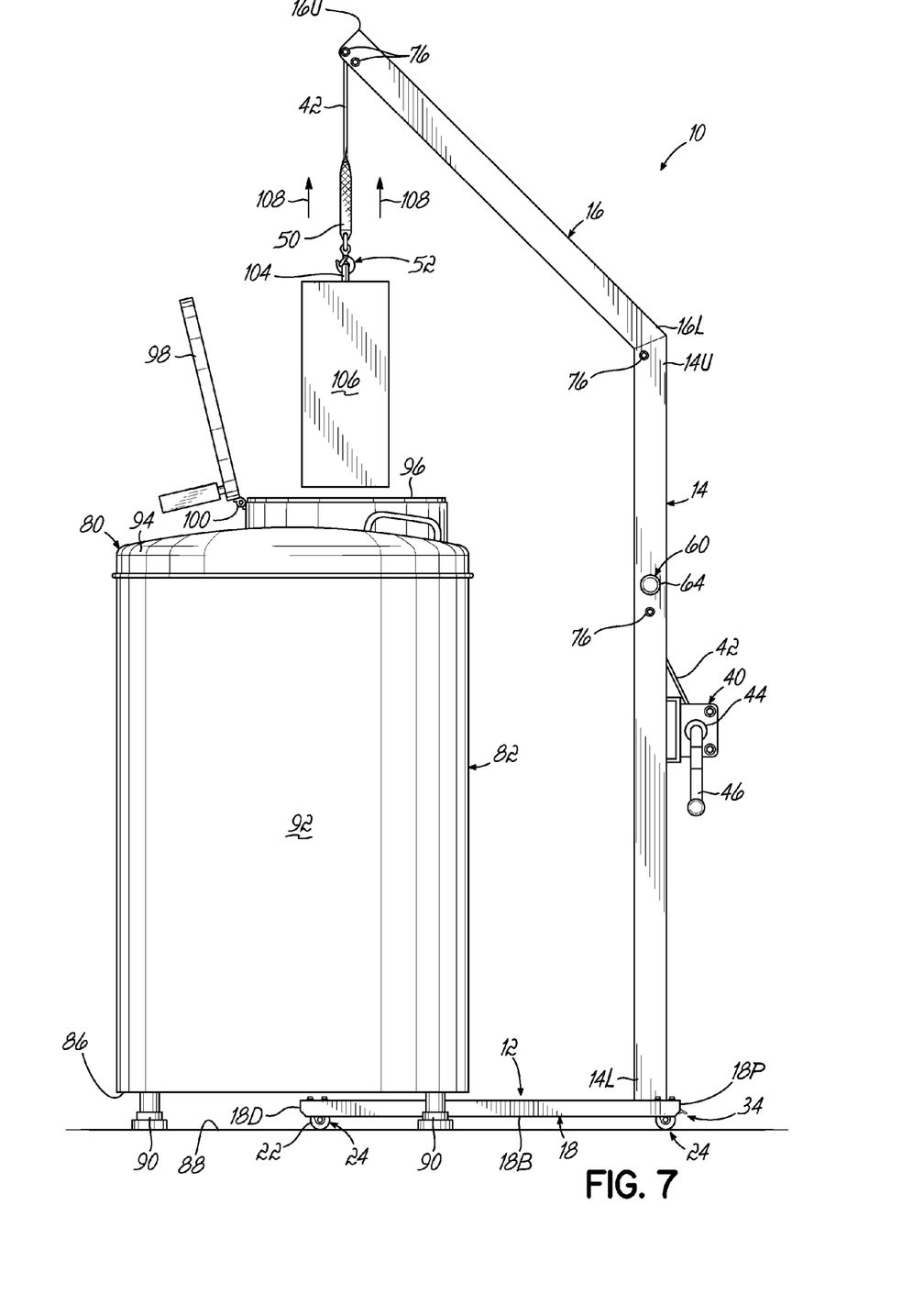
FIG. 7 is a side view of the retrieval crane and tank freezer of FIG. 6 in a third operational state of the method, in which the cable has been retracted so that the hook lifts the storage rack out of the tank freezer through the opening and holds the storage rack in a hoisted position where a user can access the storage rack.

Thus, in the third operational state shown in FIG. 7, the user has rotated the hand crank 46 in an opposite direction to cause winding up of the cable 42 onto the reel 44. This winding up of the cable 42 also pulls or retracts the free end 50 of the cable 42 and the retention hook 52 upwardly towards the upper terminal end 16U of the boom 16, as indicated by arrows 108 in FIG. 7. Once the storage rack 106 has been pulled at least partially (or completely, as shown) out of the storage space 84, the manual winch 40 and/or the hand crank 46 can be locked in position by the locking mechanism 48 described above, so as to lock the cable 42 in position and maintain the storage rack 106 in the hoisted position shown. Thus, the user can have both hands free to remove or replace items on and off the storage rack 106 while this element is reliably held in a stationary position by the crane 10.

Figure 8:
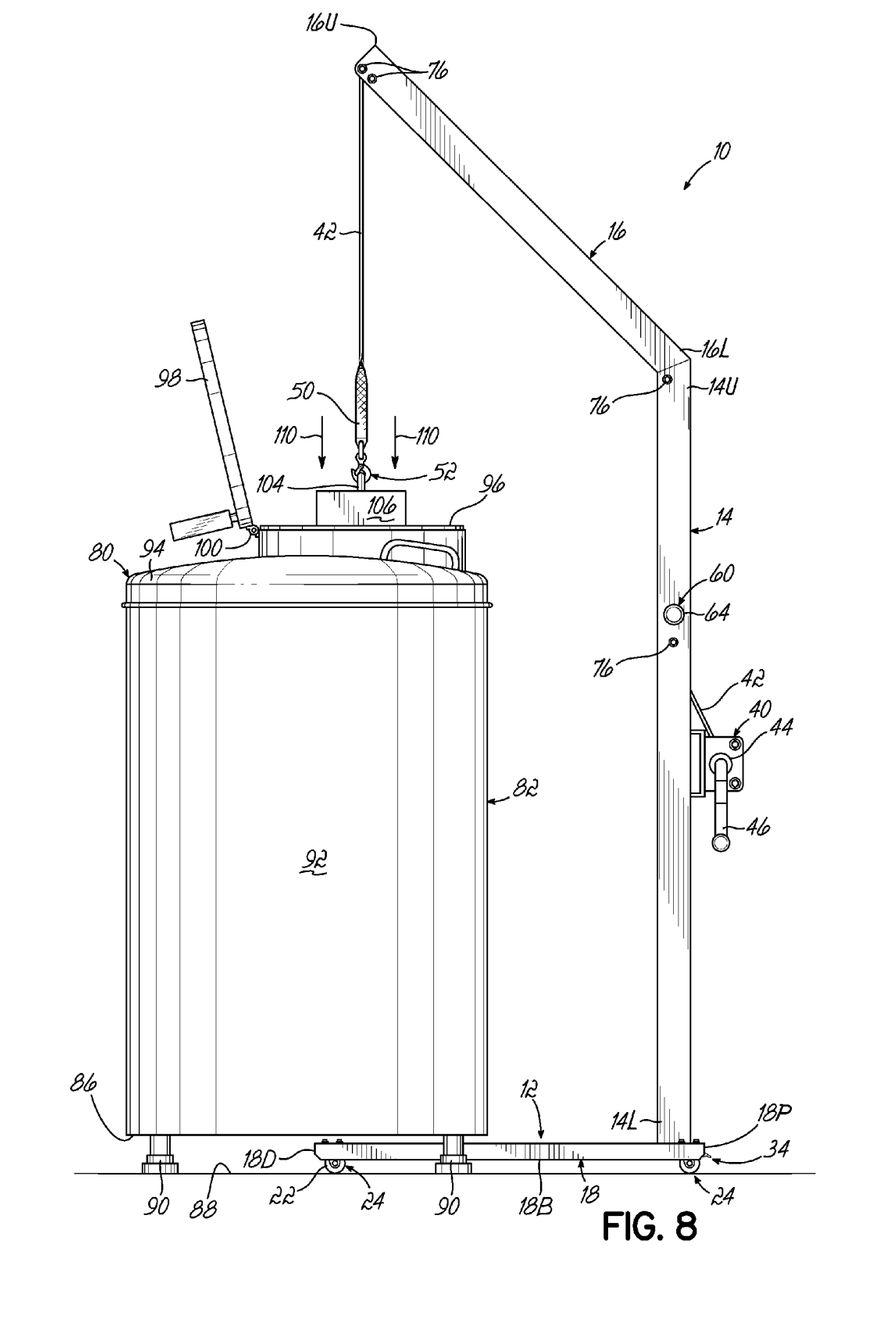
FIG. 8 is a side view of the retrieval crane and tank freezer of FIG. 7 in a fourth operational state of the method, in which the cable has been extended so that the hook lowers the storage rack back into the tank freezer through the opening.
Figure 9:
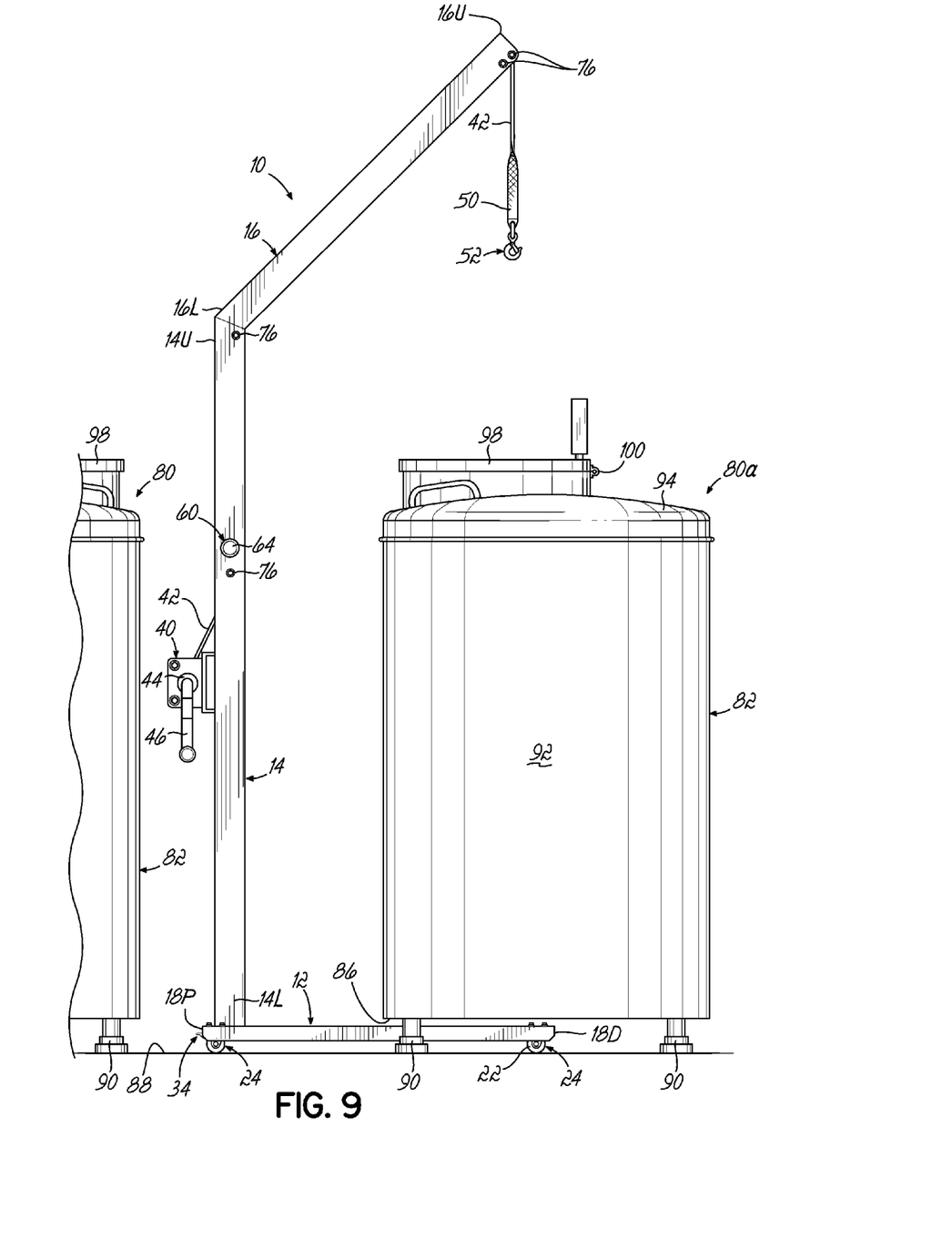
FIG. 9 is a side view of the retrieval crane and tank freezer of FIG. 8 in a fifth operational state of the method, in which the cable and hook are retracted out of the tank freezer and the retrieval crane has been repositioned adjacent to a second tank freezer so that the cable and hook are located above the opening of this second tank freezer.

Once the user is finished working with the selected storage rack 106, the locking mechanism 48 may be disengaged (if previously engaged) and the hand crank 46 may be rotated to unwind some of the cable 42 from the reel 44 again, as previously described. This unwinding of the cable 42 causes the free end 50 of the cable 42 and the retention hook 52 to be extended from or moved downwardly away from the upper terminal end 16U of the boom 16, which thereby moves the storage rack 106 back through the opening 96 into the storage space 84 of the tank freezer 80. This downward movement is indicated by arrows 110 in FIG. 8, which shows this fourth operational state of the crane 10. As will be readily understood, once the storage rack 106 is returned to the stowed position as shown in FIG. 8, the user may detach the retention hook 52 from the handle 104 on the storage rack 106 and then retract or pull the cable 42 back out of the storage space 84 so that the crane 10 is ready for use with a different tank freezer 80 or with a different storage rack 106 in the same tank freezer 80. When the crane 10 is to be moved to a different freezer, the door 98 will be closed to block the opening 96 in the tank freezer 80 following removal of the free end 50 of the cable 42 and the retention hook 52 from the storage space 84.

In the fifth and final operational state shown in accordance with this method, the retrieval crane 10 has been moved by the user (such as by pushing or pulling the handles 60) to be adjacent to a different tank freezer 80a. This second tank freezer 80a is largely identical to the first tank freezer 80 and therefore is not described in detail again herein. When the second tank freezer 80a includes a second storage rack (not shown) to be retrieved, this positioning of the crane 10 in FIG. 9 allows for the second storage rack to be retrieved using the crane 10. To this end, the base 12 and wheels 22 are at least partially rolled underneath the bottom wall 86 of the tank body 82 on the second tank freezer 80a until the upper terminal end 16U of the boom 16 is located directly above the opening 96 and door 98 of the second tank freezer 80a. Then, in accordance with the steps described previously, the free end 50 of the cable 42 and the retention hook 52 may be inserted or dropped into the storage space 84 of the second tank freezer 80a so that the second storage rack can be hoisted out of the storage space 84 similar to above. Thus, even in a facility including a large number of different tank freezers 80, 80a, etc., the single retrieval crane 10 may be used to retrieve and hoist storage racks from any number of these tank freezers 80, 80a. Thus, the crane 10 advantageously limits the work that needs to be performed by a user when accessing items in the storage racks 106 within the tank freezers 80, 80a, thereby reducing the likelihood of physical strain.

Figure 10:
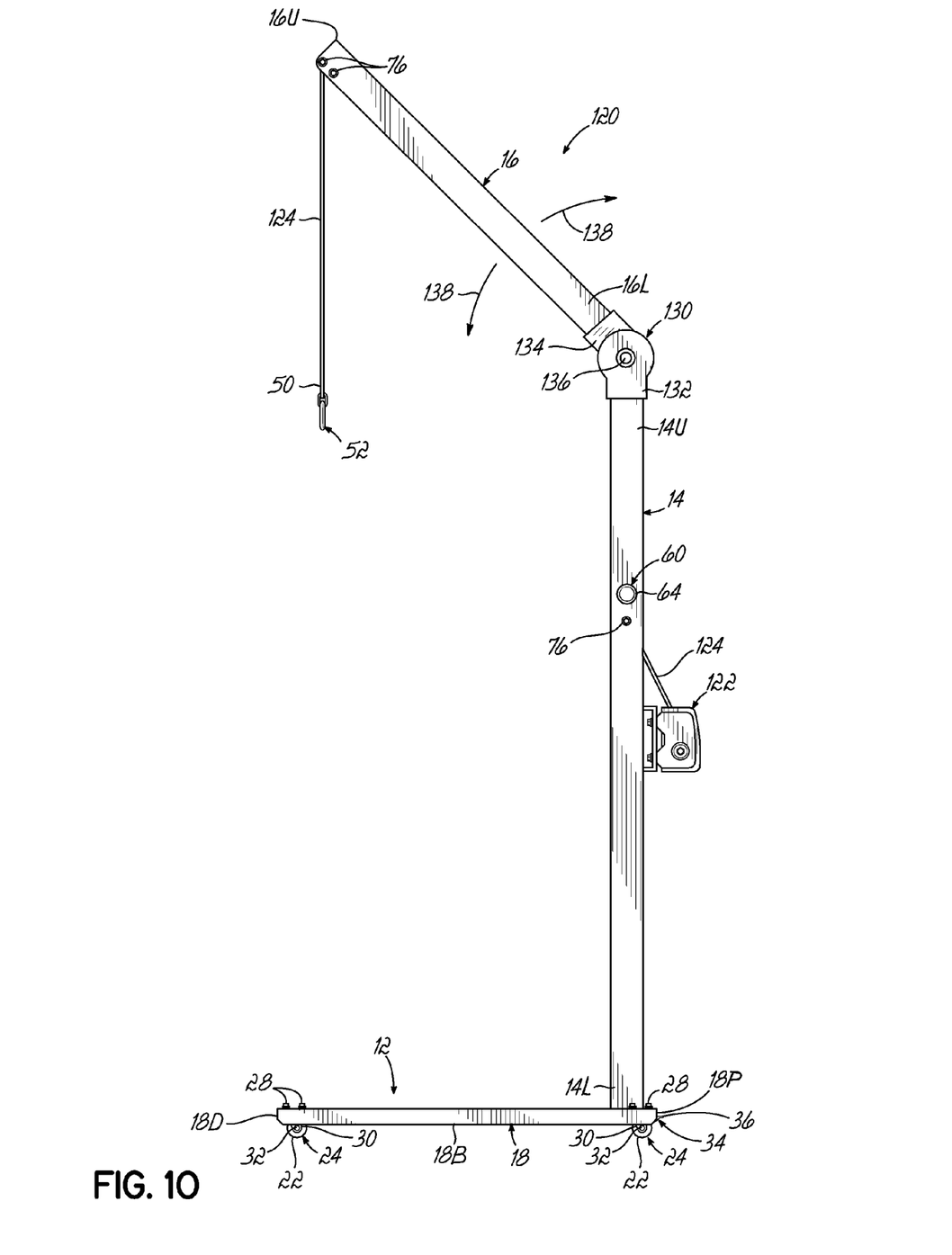
FIG. 10 is a side view similar to FIG. 2 of a retrieval crane in accordance with a second exemplary embodiment of the present invention, this crane including an electric winch and a pivoting joint between the boom and the vertical frame member.

With reference to FIG. 10, another exemplary embodiment of the retrieval crane 120 is shown. The retrieval crane 120 of this embodiment includes many of the same features as the previously-described exemplary embodiment, including the base 12, vertical frame member 14, and boom 16, and these elements have been provided with the same reference numbers where identical to the previous description. One difference of this exemplary embodiment in FIG. 10 is the replacement of the manual winch 40 with an electric winch 122, which may include the reel 44 previously described or may interact with such a reel 44 to wind up or unwind (and therefore extend or retract) the cable 124. The cable 124 in this embodiment may be a coated steel cable included with the electric winch 122 rather than the nylon strap described in the first embodiment above. In one example, the electric winch 122 is the Master Lock® 2953AT winch commercially available from www.masterlock.com. This electric winch 122 is rated for loads of up to 2000 pounds and is capable of moving the approximately 30 foot long cable 124 up to 6 feet per minute with full loading. It will be appreciated that other types of electric winches may be used in similar embodiments without departing from the scope of the present invention. When the electric winch 122 is provided, the user must simply actuate this winch 122 (such as by pressing included control buttons, for example) to move the cable 124 in accordance with the method described above.

Another difference in this exemplary embodiment shown in FIG. 10 is the addition of a pivoting joint 130 connecting the upper terminal end 14U of the vertical frame member 14 with the lower terminal end 16L of the boom 16. The pivoting joint 130 includes a first receptacle 132 coupled to the vertical frame member 14 and a second receptacle 134 coupled to the boom 16, with the first and second receptacles 132, 134 moveable relative to each other around a pivot pin 136. For example, the pivoting joint 130 may include an internal ratcheting mechanism (not shown) that enables ratcheting movement between a plurality of positions where the boom 16 is angled at different angles from the vertical frame member 14. This pivoting movement of the boom 16 is indicated schematically by arrows 138 in FIG. 10. Thus, in facilities where differently-sized tank freezers (or tank freezers with different locations for openings) are used, this embodiment of the crane 120 enables adjustment of the boom 16 so that it is ensured that the free end of the cable 124 and the retention hook 52 can be positioned directly above an opening in each type of tank freezer when the retrieval crane 120 is moved adjacent to those tank freezers. It will be understood that the features of this embodiment may be combined in any combination with the features of the first exemplary embodiment shown in FIGS. 1 through 4, without departing from the scope of the present invention.

The retrieval crane 10, 120 in accordance with the embodiments described above helps assist a user with retrieval and hoisting of storage racks, especially vertically-oriented storage racks, out of large tank freezers 80, 80a. The portability of the retrieval crane 10, 120 and the low profile defined by the base 12 and the wheels 22 enables the crane 10, 120 to be easily moved about a facility and used with different tank freezers 80, 80a. Consequently, a separate crane mechanism does not need to be provided for each tank freezer 80, 80a, but the benefits of reducing physical strain on workers. Accordingly, the retrieval crane 10, 120 addresses many of the drawbacks with the typical manual retrieval of storage racks from tank freezers, with a minimal added manufacturing cost and minimal additional steps required.

While the present invention has been illustrated by the description of exemplary embodiments thereof, and while these embodiments have been described in considerable detail, these are not intended to restrict or in any way limit the scope of the appended claims to such detail. Additional advantages and modifications will readily appear to those skilled in the art. The present invention in its broader aspects is therefore not limited to the specific details, representative apparatus and method and illustrative examples shown and described. Accordingly, departures may be from such details without departing from the scope or spirit of the general inventive concept.

What is claimed is:

1. A method for retrieving storage racks in a tank freezer, the tank freezer having a storage space defined by a tank body including a bottom wall spaced from a floor surface by at least one support, a sidewall extending upwardly from the bottom wall, and a top wall defining an opening into the storage space, the method comprising:

positioning a retrieval crane adjacent to the tank freezer such that a base of the retrieval crane is located on the floor surface and extends at least partially underneath the bottom wall of the tank body, the retrieval crane also including a boom extending upwardly and laterally over the base to an upper terminal end of the boom, and a cable running along at least a portion of the boom such that the cable is extendible or retractable to move a retention hook located at a free end of the cable relative to the upper terminal end of the boom, wherein the retrieval crane further includes wheels operatively connected to the base, and positioning the retrieval crane further comprises rolling the base and at least one of the wheels between the bottom wall and the floor surface, the wheels being operatively mounted on the base so as to be at least partially recessed in the base, such that the base fits underneath the bottom wall;

extending the cable to lower the retention hook through the opening in the tank freezer and into the storage space;

attaching the retention hook to a selected one of the storage racks within the storage space; and retracting the cable to lift the retention hook and the selected storage rack through the opening and to a hoisted position at least partially out of the tank freezer.

2. A method for retrieving storage racks in a tank freezer, the tank freezer having a storage space defined by a tank body including a bottom wall spaced from a floor surface by at least one support, a sidewall extending upwardly from the bottom wall, and a top wall defining an opening into the storage space, the method comprising:

positioning a retrieval crane adjacent to the tank freezer such that a base of the retrieval crane is located on the floor surface and extends at least partially underneath the bottom wall of the tank body, the retrieval crane also including a boom extending upwardly and laterally over the base to an upper terminal end of the boom, and a cable running along at least a portion of the boom such that the cable is extendible or retractable to move a retention hook located at a free end of the cable relative to the upper terminal end of the boom;

extending the cable to lower the retention hook through the opening in the tank freezer and into the storage space;

attaching the retention hook to a selected one of the storage racks within the storage space;

retracting the cable to lift the retention hook and the selected storage rack through the opening and to a hoisted position at least partially out of the tank freezer;

extending the cable to lower the retention hook and the selected storage rack through the opening back into the storage space;

detaching the retention hook from the selected storage rack such that the retrieval crane is ready for use in retrieving a different storage rack;

moving the retrieval crane away from the tank freezer and adjacent to a second tank freezer containing a second selected storage rack to be retrieved within a storage space; and inserting the free end of the cable and the retention hook into the storage space of the second tank freezer to prepare the second selected storage rack to be hoisted out of the storage space by the retrieval crane, wherein a single retrieval crane may be used to retrieve and hoist storage racks in any number of a plurality of tank freezers.

3. The method of claim 1, further comprising:
locking the cable in position to maintain the selected storage rack in the hoisted position while samples are retrieved from or placed into the storage rack.

4. The method of claim 1, wherein the retrieval crane further includes wheels operatively connected to the base, and positioning the retrieval crane further comprises:
rolling the base and at least one of the wheels between the bottom wall and the floor surface, the wheels being operatively mounted on the base so as to be at least partially recessed in the base, such that the base fits underneath the bottom wall.

5. The method of claim 4, wherein positioning the retrieval crane further comprises:
locking the wheels with at least one locking brake associated with the wheels after rolling the base between the bottom wall and the floor surface, the at least one locking brake maintaining the position of the retrieval crane relative to the tank freezer during use of the cable and the retention hook.

6. The method of claim 1, wherein the cable of the retrieval crane is wound about a reel at an opposite end from the free end, and each of extending and retracting the cable further comprises:
rotating a hand crank coupled to the reel to wind up or unwind the cable, thereby moving the free end of the cable relative to the upper terminal end of the boom.

7. The method of claim 6, further comprising:
engaging a locking mechanism with the hand crank to prevent further rotation of the hand crank in either direction and also to prevent movement of the free end of the cable relative to the boom.

8. The method of claim 2, wherein the cable of the retrieval crane is wound about a reel at an opposite end from the free end, and each of extending and retracting the cable further comprises:
actuating an electric winch connected to the reel to wind up or unwind the cable, thereby moving the free end of the cable relative to the upper terminal end of the boom.

9. The method of claim 2, wherein the retrieval crane further includes a generally vertical frame member extending between the base and the boom, and positioning the retrieval crane further comprises:
at least one of pushing and pulling a set of handles projecting laterally from the vertical frame member until the upper terminal end of the boom is located directly above the opening in the tank freezer.

10. The method of claim 2, wherein the retrieval crane further includes a generally vertical frame member extending between the base and the boom, the vertical frame member and the boom being connected by a pivoting joint, and positioning the retrieval crane further comprises:
ratcheting the pivoting joint to rotate the boom relative to the base to thereby adjust how far the base has to be inserted underneath the bottom wall of the tank freezer to position the upper terminal end of the boom directly over the opening in the tank freezer.

* * * * *